United States Patent [19]
Dehnert

[11] 4,119,090
[45] Oct. 10, 1978

[54] ELECTROCARDIOSCOPE

[76] Inventor: Heinz Dehnert, Am Bahnhof, D-7801 Hugstetten-March, Fed. Rep. of Germany

[21] Appl. No.: 792,830

[22] Filed: May 2, 1977

[30] Foreign Application Priority Data

Jun. 1, 1976 [DE] Fed. Rep. of Germany ....... 2624581

[51] Int. Cl.² .............................................. A61B 5/04
[52] U.S. Cl. ........................... 128/2.06 G; 346/33 ME
[58] Field of Search ..................... 128/2.05 Q, 2.06 G, 128/2.06 R, 2.06 V; 346/33 ME

[56] References Cited

U.S. PATENT DOCUMENTS

| | | | |
|---|---|---|---|
| 2,933,364 | 4/1960 | Campbell | 128/2.1 B |
| 3,585,988 | 6/1971 | Creigh et al. | 128/2.06 G |
| 3,707,147 | 12/1972 | Sellers | 128/2.06 G |
| 3,793,626 | 2/1974 | Zambuto | 128/2.06 R |
| 3,799,148 | 3/1974 | Rowen | 128/2.06 G |
| 3,990,435 | 11/1976 | Murphy | 346/33 ME |

*Primary Examiner*—William E. Kamm
*Attorney, Agent, or Firm*—Pollock, Vande Sande and Priddy

[57] ABSTRACT

An electrocardioscope with an input amplifier amplifying the analog ECG signals, with an output Y-amplifier for the Y-deflection and an X-output amplifier for the X-deflection. Between the input amplifier and the output Y-amplifier an analog digital converter, a memory with N-addresses and M-memory values per address and a digital analog counter are arranged. The address selection is determined at the memory by an address generator with N-sites. The input of the output X-amplifier is connected with the digital analog converter and the input of the latter is connected with an X-counter with selectively settable N- and N+n-count digits and the address generator and the X-counter are clocked by a clock.

10 Claims, 1 Drawing Figure

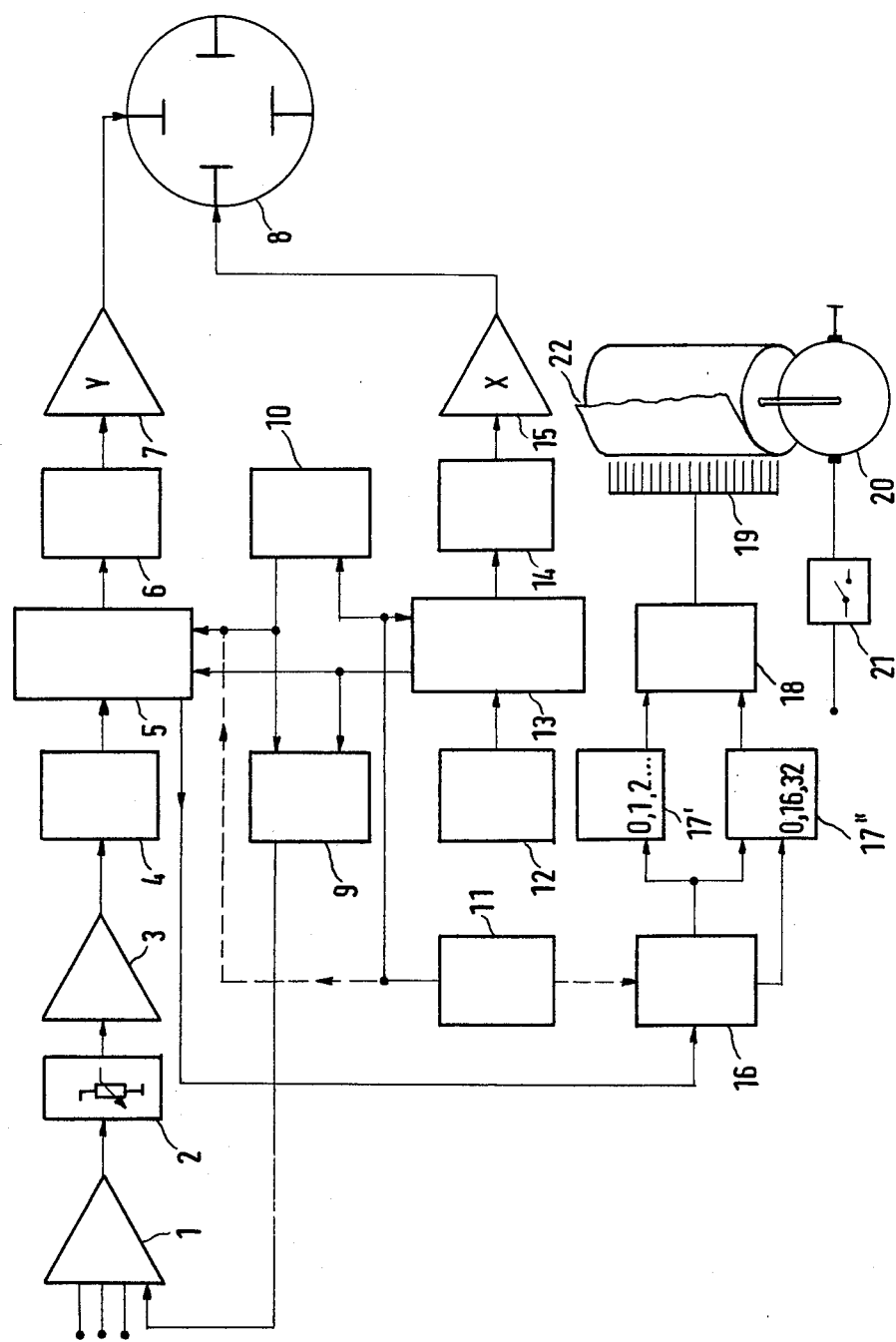

ELECTROCARDIOSCOPE

BACKGROUND OF THE INVENTION (1) Field to which the invention relates

The invention relates to an electrocardioscope with an input amplifier amplifying the analog ECG signal, an output Y-amplifier determining the Y-deflection of the display tube and an output X-amplifier determining the X-deflection.

(2) The prior art

In the case of prior art electrocardioscopes the electron beam of the display tube moves as a bright spot from the left to the right on the picture screen. In order to be able to follow the ECG curve the picture screen has a relatively high persistence.

Portable electrocardioscopes have already been proposed. On the bottom of such an electroscope two or three electrodes are provided which contact the chest of the patient and the cardioscope is placed on it. The power supply is in the form of primary cells or accumulators.

Furthermore ECG recorders have been provided with which the curve of the ECG can be recorded on a recording paper. In this respect, however, it is usually a question of stationary equipment in the case of which the electrodes are connected with the patient using extremity cables.

Furthermore a portable electrocardiograph has been proposed whose bottom is provided with the above mentioned electrodes and which is therefore to be placed on the chest of the patient. By means of a thermosensitive recording paper the ECG curve can be recorded. It is a disadvantage in this respect that it is only after a certain time that the recorded curve becomes visible so that an immediate starting of the shape of the curve even during the act of recording is not possible.

SHORT SUMMARY OF THE INVENTION

The present invention is concerned with an improved apparatus for investigating and monitoring an ECG wherein the ECG curve is visible for its whole extent and more particularly is in existence as a standing or stationary image so that it can be analysed in detail. The apparatus is also able to record characteristic curves.

DESCRIPTION OF PREFERRED EMBODIMENT OF THE INVENTION

One embodiment of the invention is shown in the accompanying FIGURE of the drawing, which shows a block circuit diagram of an electrocardioscope.

The ECG signal supply through three electrodes is amplified in an input amplifier 1. The invention is not limited to three electrodes, the number only being chosen by way of example. The block 2 serves for setting the amplified signal amplitude and the signal is supplied then to an impedance converter in the form of an intermediate amplifier 3. The analog ECG signal at the output of the amplifier 3 is then supplied to an analog digital converter 4, which converts the analog data in digital data. The digital data of the ECG signal are given to a memory 5, and then passed on from the latter to a digital analog converter 6. In this digital analog converter the digital stored data are converted back into analog data, which are then supplied to an output Y-amplifier 7. The analog signals at the output of the output amplifier 7 determine the vertical deflection at the screen of CRT tube 8.

The address selection at the memory 5 is brought about by an address generator 10, which is clocked by a clock 11.

The sequence of the input and output of the digital values into and from the memory 5 is determined by an X-counter 13 which is also clocked by the clock 11. This X-counter 13 simultaneously determines the horizontal deflection in the CRT tube 8. For this purpose the X-counter 13 is connected with a digital analog converter 14, whose output is in turn connected with the input of the output X-amplifier 15. The output of this amplifier 15 is connected with the deflecting electrodes, determining the horizontal deflection, of the tube 8.

The manner of operation of the construction just described is as follows: The memory 5 has for example N-addresses (e.g. 512 addresses), and each address has M storage or memory values (e.g., 256 memory values). The address generator 10 has N-sites so that coming one after the other from the address generator 10 the N-addresses of the memory 5 are selected. The X-counter 13 can be set as regards its digits. By means of the block 12 it is possible to set selectively N or N+n-digits in the counter 13. For this purpose the respective N-digits are determinative for the output of the memory data from the memory 5, while the n-counter digits occurring with the count digit setting N+n determine the erasing and rerecording of stored data of the addresses respectively selected by the address generator 10.

If the counter 13 is set at N-counting digits, then in synchronism with the address generator 10 each address of the memory 5 is connected with the digital analog converter 6. In this manner a standing or stationary image is produced at the CRT tube 8 of the curve as stored in the memory 5. Rerecording of the memory data does not occur when this is done. In this manner the curve stored in the memory 5 can be exactly analyzed.

If the counter 13 on the other hand has N+n-counting digits and if for example N is equal to 1, the device operates as follows: During the counting up to N the N-addresses, selected by the address generator 10, are connected one after the other with the digital analog converter 6. If the address generator 10 begins its cycle again with the first selection pulse, then on the selection of this address the X-counter 13 provides its N+1-pulse so that the content of this selected address is erased and this address of the memory 5 is connected with the analog digital converter 4. In this manner therefore on every cycle of the address generator 10 one address is erased in the memory 5 and provided with a new value to be stored. In the subsequent cycle of the address generator 10 a respectively adjacent address is therefore erased and in it a new value is stored.

The clock 11 can be switched over to different clock times or frequencies, that is to say in accordance with transit speeds of 12.5, 25 or 50 mm per second. By connecting the X-counter 13 with the horizontal deflection circuitry in the CRT screen tube 8 on each cycle of the address generator 10 the image is therefore displaced by one horizontal image point to the left. In the case of a deflection of 50 mm per second corresponding to 400 Hz there is therefore a displacement by 400 image points per second. In the case of a deflection of 25 mm per second corresponding to 200 Hz there is a displacement of 200 image points per second while at 12.5 mm per second the displacement amounts to 100 image points per second.

In order to be able to evaluate the size of the ECG signal a constant voltage source 9 is provided, which is connected with an input amplifier 1. This constant voltage source 9 can be connected with the address generator 10 and with the X-counter 13 in order in this manner to bring about a pulse-like issue of calibration signals to the input amplifier 1. In this manner it is possible to carry out an overall check of the electrocardioscope including its frequency behavior.

In order to be able to record ECG data stored in the memory 5, the electrocardioscope is provided with a writing device, which forms an integral component of the transportable device. The writing device consists in this respect of an electrode comb 19, which has a paper strip 22 moving along underneath it. The respective energized electrode of the electrode comb 19 produces a scorch dot on the paper 22. Preferably it is an aluminum coated paper 22.

The memory 5 is connected with an optocoupler 16, which for its part drives a decoder circuit 17' and 17", which acts on a network matrix 18 for timed driving of the electrodes of the comb 19. In order to keep paper consumption in the direction of writing within reasonable limits, the current supply line for the motor 20 of the paper advance system comprises a timing switch 21. On switching on the motor 20 the latter continues to run until a length of paper of approximately 50 mm has been transported. Owing to the overall arrangement it is possible to record, by pressing a push button, such ECG curves, as are particularly relevant for the respective patient.

During operation of the recording device it is possible for the clock 11 to clock the memory directly. The addresses, selected by the clock 11, of the memory 5 are then directly supplied to the optocoupler 16.

Since the memory 5 generally has more addresses than the comb 19 electrodes, the circuit arrangement can be such that the clock 11 do not serve to couple all addresses with the optocoupler 16 but only certain addresses. If for example the memory 5 has 512 addresses and if the electrode comb 19 has 64 electrodes then on scanning the respective eighth address of the memory 5 is connected with the optocoupler 16, while the intermediate seven addresses are left out of consideration. This address selection can also be carried out using a selector switch which is not shown.

The optocoupler 16 is also clocked by the clock 11. Its output values or signals are decoded in the decoder 17' and 17" both as regards their position and also as regards amplitude, and the amplitude decoding is linked with the time position decoding in a network matrix 18. If during the writing operation the clock 11 directly clocks the memory 5, this clock frequency can differ from the frequency which serves for clocking the address generator 10 and of the X-counter 13. The direct clocking can, however, readily be dropped.

The device as a whole is accommodated in a portable housing on which at the bottom the electrodes are arranged while on the front side the screen of the CRT tube is arranged. The device is operated by primary cells or by accumulators. The electrodes can be arranged in a plate, which can be plugged to the bottom side of the device.

A substantial advantage is the saving in recording paper and working time during evaluation for only really relevant curve sections or operating conditions of the heart are registered, which had previously been recognized on the display screen.

With the circuitry described above it is more particularly also possible to record only separate sections of the ECG curve. By suitable switching over it is possible, using for example a writing comb with for example 64 electrodes, to supply 64 addresses occurring one after the other in the memory 5 or, of 128 addresses occurring one after the other, the second respective address to the optocoupler 16. For this purpose the ECG curve moving from the left to the right on the screen of CRT tube 8 is stopped at that position in the curve, which represents the beginning of the curve part which is to be recorded. Then the recording button is depressed and the respective image points (for example each one, each second one or each third one, etc.) are transferred by a suitable address selection in the counter 5 to the registering system and respectively the optocoupler 16.

What I claim is:

1. An electrocardioscope comprising an input amplifier for amplifying an analog ECG signal, a display tube, an output Y-amplifier having its output coupled to said display tube for determining the Y-deflection of said display tube, an output X-amplifier having its output coupled to said display tube for determining the X-deflection of said display tube, an analog to digital converter coupled to the output of said input amplifier, a memory coupled to the output of said converter, said memory having N-addresses and M-memory values per address, a digital to analog converter connected between the output of said memory and the input of said Y-amplifier, means for effecting address selection at the memory comprising an address generator with N-sites coupled to said memory, a further digital to analog converter having its output connected to the input of said output X-amplifier, an X-counter having its output connected to the input of said further digital to analog converter, means connected to said X-counter for selectively setting N- and N+n-count digits into said counter, and clock means coupled to said address generator and to said X-counter for clocking said address generator and said counter.

2. An electrocardioscope in accordance with claim 1, including means for selectively setting the frequency of said clock means to any one of a plurality of different clock frequencies.

3. An electrocardioscope in accordance with claim 2 wherein said setting means is operative to set the frequency of the clock to an image scanning frequency of 400, 200 or 100 Hz, to produce a deflection speed of 50, 25 or 12.5 mm per second at said display tube.

4. An electrocardioscope in accordance with claim 1, wherein $n$ is equal to 1.

5. An electrocardioscope in accordance with claim 1, wherein said X-counter is connected to said memory and being operative during counting of the N-count digits to connect the respective address of the memory selected by the address generator to said digital analog converter, said X-counter being operative during counting of the $n$-count digits to erase the respectively selected address of the memory and to connect said selected address to the output of the analog to digital converter.

6. An electrocardioscope in accordance with claim 1 including a constant voltage source connected to said X-counter, said constant voltage source cooperating with the X-counter to supply signals of constant amplitude to the input amplifier for purposes of calibration.

7. An electrocardioscope in accordance with claim 1 wherein the memory has 512 addresses and 256 memory values per address.

8. An electrocardioscope in accordance with claim 1 including means for recording an ECG curve, said recording means comprising a supply of paper, a writing electrode comb adjacent said paper, a matrix connected to said comb, a decoder connected to said matrix, and means for connecting said decoder to the memory, the memory and the decoder being connected to and clocked by the clock means.

9. An electrocardioscope in accordance with claim 8, including a paper advance motor coupled to said paper supply, and a timer for selectively de-energizing said motor to discontinue the feed of paper from said supply after a predetermined quantity of paper has been fed.

10. An electrocardioscope in accordance with claim 8, wherein said means for connecting said decoder to the memory comprises an optocoupler between the memory and the decoder, said optocoupler being connected to and clocked by said clock means.

* * * * *